(12) United States Patent
Ni et al.

(10) Patent No.: US 6,746,674 B2
(45) Date of Patent: Jun. 8, 2004

(54) CYTOSTATIN II

(75) Inventors: Jian Ni, Germantown, MD (US);
Guo-Liang Yu, Berkeley, CA (US);
Reiner L. Gentz, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/971,187

(22) Filed: Oct. 5, 2001

(65) Prior Publication Data

US 2002/0031804 A1 Mar. 14, 2002

Related U.S. Application Data

(62) Division of application No. 09/043,646, filed as application No. PCT/US95/12540 on Sep. 29, 1995, now Pat. No. 6,329,169.

(51) Int. Cl.⁷ ........................ A61K 39/00; C07K 14/715
(52) U.S. Cl. ................. 424/192.1; 530/351; 530/402; 536/23.5
(58) Field of Search ........................ 530/351; 536/23.5

(56) References Cited

U.S. PATENT DOCUMENTS 5,194,596 A * 3/1993 Tischer et al. ............... 530/399
5,350,836 A * 9/1994 Kopchick et al. ........... 530/399

FOREIGN PATENT DOCUMENTS

| DE | 43 38 817 A1 | 11/1993 |
| JP | 10-286089 | 10/1998 |
| WO | WO94/01548 | 1/1994 |
| WO | WO97/11970 A1 | 4/1997 |
| WO | WO98/45440 A1 | 10/1998 |

OTHER PUBLICATIONS

Vukicevic et al. 1996, PNAS USA 93:9021–9026.*
Shi et al., Database SwissProt_40, Accession No. 015540, submitted Dec. 1996.*
Shi et al., Database SwissProt_40, Accession NO. 015540, submitted Dec. 1996.*
Hillier et al., GenBank Accession No. H46792, Jul. 31, 1995.
Yang et al., "Members of the Fatty Acid Binding Protein Family . . . ," Journal of Cell Biology, 127 (4):1097–1109, Nov. 1994.
Peeters et al., "Cloning of the cDNA encoding human skeletal–muscle," Biochem Journal, 276:203–207, 1991.
Peeters et al., "Expression in *Escherichia coli* and characterization of the fatty–acid–binding . . . ," Biochem Journal, 278:361–364, 1991.
Hillier et al., GenBank Accession No. W76403, Jun. 23, 1996.
De Leon et al., "Fatty Acid Binding Protein Is Induced in Neurons . . . ," J. of Neuroscience Research, 44:283–292, 1996.
Bohmer et al., "Identification of a Polypeptide Growth Inhibitor . . . ," Journal of Biological Chemistry, 262 (31):15137–15143, Nov. 5, 1987.
Hillier et al., GenBank Accession No. R60348, May 24, 1995.
Godbout, "Identification and Characterization of Transcripts . . . ," Exp. Eye Res., 56:95–106, 1993.
Godbout, Genbank Accession No. X65459, Sep. 15, 1993.
Godbout, Genbank Accession No. Q05423, Oct. 1, 1996.
Shimizu et al., "Isolation and expression of a cDNA for human brain fatty acid–binding protein (B–FABP)," Biochimica et Biophysica Acta, 1354:24–28, 1997.
Kim et al., "Tetramerization of an RNA oligonucleotide containing a GGGG sequence," Letters to Nature, 351:331–332, 1991.
Burton et al., "Heart Fatty Acid Binding Protein Is A Novel Regulator of Cardiac Myocyte Hypertrophy," Biochemical and Biophysical Research Communications, 205(3):1822–1828, Dec. 30, 1994.
Grosse et al., "5. Mammary–Derived Growth Inhibitor (MDGI)," Dickson et al., Genes, Oncogenes, and Hormones: Advances in Cellular and Molecular Biology of Breast Cancer, Kluwer Academic Publishers, Boston, 1991.
Feng et al., "Brian Lipid–Binding Protein (BLBP): . . . ," Neuron, 12:895–908, Apr. 1994.
Kleine et al., "Release of heart fatty acid–binding protein into plasma after acute myocardial infarction in man," Molecular and Cellular Biochemistry, 116:155–162, 1992.
Kurtz et al., "The expression pattern of a novel gene encoding brain–fatty acid binding . . . ," Development, 120:2637–2649, 1994.
Kurtz et al., "Developmental Regulation of Mammary–derived Growth Inhibitor . . . ," Journal of Cell Biology, 110:1779–1789, May 1990.
Treuner et al., "Cloning and characterization of the mouse gene encoding . . . ," Gene, 147:237–242, 1994.
Ngo et al., "Computational Complexity, Protein Structure Prediction, and the Levinthal Paradox," The Protein Folding Problem and Tertiary Structure Prediction, Mertz et al., Birkhauser Boston, 433–395, 1994.
Huynh et al., "Tumor Suppressor Activity of the Gene Encoding Mammary–derived Growth Inhibitor," Cancer Research, 55:2225–2231, Jun. 1, 1995.
Hillier et al., GenBank Accession No. N57521, Feb. 22, 1996.

(List continued on next page.)

*Primary Examiner*—Yvonne Eyler
*Assistant Examiner*—Eileen O'Hara
(74) *Attorney, Agent, or Firm*—Human Genome Sciences, Inc.

(57) ABSTRACT

The invention relates to cytostatin II growth modulatory polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

58 Claims, 1 Drawing Sheet

OTHER PUBLICATIONS

Hillier et al., GenBank Accession No. N47671, Feb. 14, 1996.

Siegenthaler et al., "Purification and characterization of the human epidermal fatty acid–binding protein . . . ," Biochem. J., 302:363–371.

Veerkamp et al., "Structural and functional features of different types of cytoplasmic fatty acid–binding proteins," Biochimica et Biophysica Acta., 1081:1–24, Jan. 4, 1991.

Veerkamp and Maatman, "Cytoplasmic Fatty Acid–Binding Proteins: Their Structure and Genes," Pro. Lipid Res., 34(1):17–52, 1995.

Hillier et al., The WashU–Merck EST Project, Accession No. H46792.

Benjamin et al., "A plasticity window for blood vessel remodelling is defined by pericyte coverage . . . ," Development, 125:1591–1598, 1998.

Vukicevic et al., "Induction of nephrogenic mesenchyme by osteogenic protein 1 . . . ," Proc. Natl. Acad. Sci. USA, 93:9021–9026, 1996.

Massague, J., "The TGF–beta Family of Growth and Differentiation Factors," Cell. 49:437–438, May 22, 1987.

Pilbeam et al., "Comparison of the Effects of Various Lengths of Synthetic Human Parathyroid . . . ," Bone, 14:717–720, 1993.

Bowie et al., "Deciphering the Message in Protein Sequences . . . ," Science, 247:1306–1310, Mar. 16, 1990.

* cited by examiner

```
          10                  30                  50
GGGGAAAGGGCAAGGATGGTGGAGGCTTTCTGTGCTACCTGGAAGCTGACCAACAGTCAG
              M  V  E  A  F  C  A  T  W  K  L  T  N  S  Q
          70                  90                 110
AACTTTGATGAGTACATGAAGGCTCTAGGCGTGGGCTTTGCCACTAGGCAGGTGGGAAAT
 N  F  D  E  Y  M  K  A  L  G  V  G  F  A  T  R  Q  V  G  N
         130                 150                 170
GTGACCAAACCAACGGTAATTATCAGTCAAGAAGGAGACAAAGTGGTCATCAGGACTCTC
 V  T  K  P  T  V  I  I  S  Q  E  G  D  K  V  V  I  R  T  L
         190                 210                 230
AGCACATTCAAGAACACGGAGATTAGTTTCCAGCTGGGAGAAGAGTTTGATGAAACCACT
 S  T  F  K  N  T  E  I  S  F  Q  L  G  E  E  F  D  E  T  T
         250                 270                 290
GCAGATGATAGAAACTGTAAGTCTGTTGTTAGCCTGGATGGAGACAAACTTGTTCACATA
 A  D  D  R  N  C  K  S  V  V  S  L  D  G  D  K  L  V  H  I
         310                 330                 350
CAGAAATGGGATGGCAAAGAAACAAATTTTGTAAGAGAAATTAAGGATGGCAAAATGGTT
 Q  K  W  D  G  K  E  T  N  F  V  R  E  I  K  D  G  K  M  V
         370                 390                 410
ATGACCCTTACTTTTGGTGATGTGGTTGCTGTTCGCCACTATGAGAAGGCATAAAAATGT
 M  T  L  T  F  G  D  V  V  A  V  R  H  Y  E  K  A  *
         430                 450                 470
CCCTGGTCGGGGCTTGGAAGAGCTCTTCAGTTTTTCTGTTTCCTCAAGTCTCAGTGCTAT
                      490                 510                 530

CCTATTACAACATGGCTGATCATTAATTAGAAGGTTATCCTTGGTGTGGAGGTGGAAAAT 550                 570                 590
GGTGATTTAAAAACTTGTTACTCCAAGCAACTTGCCCAATTTTAATCTGAAAATTTATCA 610                 630                 650
TGTTTTATAATTTGAATTAAAGTTTTGTCCCCCCCCCCTTTTTTTTTATAAACAAGTGAAT 670                 690                 710
ACATTTTATAATTTCTTTTGGAATGTAAATCAAATTTGAATAAAAATCTTACACGTGAAA

730
AAAAAAAAAAA
```

FIG. 1

CYTOSTATIN II

This application is a divisional of U.S. application Ser. No. 09/043,646, filed Sep. 9, 1998. (now U.S. Pat. No. 6,329,169, issued Dec. 11, 2001) which is a National Stage filing of International Application No. PCT/US95/12540, filed Sep. 29, 1995, which was published in English on Apr. 3, 1997 as International Publication No. WO97/11970, which are both hereby incorporated by reference in their entiret This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human cytostatin II.

BACKGROUND OF THE INVENTION

The growth and differentiation of cells and the development of tissues and glands is controlled by autocrine and paracrine factors, such as systemic hormones and factors that modulate or mediate the action of hormones, such as growth factors, which themselves may be hormones.

For example, peptides that locally signal growth cessation and stimulate differentiation of cells of the developing epithelium are very important to mammary gland development. These factors largely have not been identified or characterized, particularly not in humans.

A few factors that play a role in the humoral mediation of growth and differentiation of cells in tissues and glands, mammary glands in particular, have been identified in non-human organisms. One such factor is mammary-derived growth inhibitor ("MDGI"), which, at least in mice and cows, inhibits epithelial cell growth and stimulates epithelial cell differentiation. MDGI was first identified in milk and mammary glands of cows. Subsequently, it was identified in mice.

MDGI occurs in at least two forms produced by alternative routes of post-translational processing. The original form is referred to as MDGI and the second form is called MDGI-2.

MDGI is associated primarily with milk fat globule membranes ("MFGM"), as assessed by immunological assays using anti-MDGI antibodies. Similar time course studies show that MDGI increases dramatically in mammary glands when lactation begins, following delivery. MDGI-2 differs from MDGI in this respect. It is found in mammary glands during pregnancy but not during lactation.

The roles of the two forms of MDGI and their mechanism(s) of action are not clearly defined. Mouse and bovine MDGI are homologous to one another and to a family of low molecular mass hydrophobic ligand-binding proteins ("low MW HLBP(s)"), which includes fatty acid-binding proteins ("FABP(s)") from brain, heart, liver and intestine, myelin P2 protein, the differentiation associated protein of adipocytes called p422 gastrotropin and cellular retinoic acid-binding protein ("CRABP"). These proteins, which bind hydrophobic ligands such as long-chain fatty acids, retinoids and eiconsanoids, are thought to play roles in the transport, sequestration, or metabolism of fatty acids and fatty acid derivatives. However, they are expressed in a differentiation specific manner, in cells of the mammary gland, heart, liver, brain and intestine, and they appear not only to play roles in basal metabolism but also to have important roles in differentiation and development.

The homology of MDGI to the low MW HLBPs raises the possibility that MDGI, at least as part of its function, binds a hydrophobic ligand, and that binding to this ligand is important to the mechanisms by which MDGI inhibits cell growth and stimulates differentiation; although all the other low MW HLBPs except gastrotropin act intracellularly, whereas MDGI acts extracellularly, in vitro.

Among the low MW HLBPs, MDGI most closely resembles the fatty acid binding proteins ("FABP"). FABPs have been identified in brain, heart, liver and intestine. Heart FABP, like MDGI, whether produced from natural sources or by expression of a cloned gene in a heterologous host, inhibits growth of normal mammary epithelial cells ("MEC") of mouse origin. In addition, it stimulates milk protein synthesis and it stimulates its own expression in these cells. However, unlike bovine heart FABP, bovine MDGI does not bind fatty acids, although the two proteins are 95% homologous and it has been suggested that heart FABP actually may be a form of MDGI. Thus, even if MDGI is a low MW HLBP, its substrate affinities are distinct from its close relatives in the family, and it therefore likely plays a different physiological role.

In vivo MDGI is found in capillary endothelial cells and in the mammary parenchyma, in mice and cows. MDGI appears first in the capillary endothelial cells and later in the secretory epithelial cells. The location of MDGI in the mammary capillary endothelium is consistent with a role in regulating endothelial cell proliferation.

A number of activities of MDGI have been demonstrated in vitro. For instance, it has been shown that MDGI inhibits L(+)-lactate-, arachidonic acid- and 15-S-hydroxyeicosatetraenoic acid-induced supersensitivity of neonatal rat heart cells to beta-adrenergic stimulation. The induced hypersensitivity is mediated by a small population of beta 2-adrenergic receptors and, therefore, it has been suggested that MDGI interferes with the normal function of these receptors. Interaction with these receptors might also be part of the mechanism by which MDGI inhibits cells growth. This activity also raises the possibility that MDGI naturally modulates the beta-adrenergic sensitivity of cardiac myocytes The effect of MDGI on differentiation of mammary epithelial cells ("MEC") has been further demonstrated by antisense inhibition experiments using phosphorothioate oligonucleotides. These experiments show that MDGI antisense molecules decrease beta-casein levels and suppress the appearance of alveolar end buds in organ cultures. Furthermore, MDGI suppresses the mitogenic effects of epidermal growth factor, and epidermal growth factor antagonizes the activities of MDGI. MDGI is the first known growth inhibitor which promotes mammary gland differentiation.

The regulatory properties of MDGI can be fully mimicked by an 11-amino acid sequence, which is represented in the carboxyl terminus of MDGI and a subfamily of the low MW HLBPs.

Not all mammary epithelial cell lines respond to MDGI in the same way. MDGI inhibits growth of normal human MEC, passaged for varying lengths of time. It also inhibits growth of the mouse mammary malignant epithelial cell lines mMaCa 20177, the human malignant mammary cell lines MaTu and T47D and it inhibits the resumption of growth of stationary Ehrlich ascites carcinoma cells ("EAC") in vitro. In contrast, MDGI slightly stimulates growth of the human malignant mammary epithelial cell line MCF7. Finally, MDGI promotes differentiation of mouse pluripotent embryonic stem cells.

The mechanism of the effects of MDGI on cells is not known, as yet. The resumption of growth of stationary Ehrlich ascites carcinoma cells ("EAC") in vitro is accompanied by a rapid increase in cellular c-fos, c-myc and c-ras mRNA. The rapid induction of these genes upon exposure to MDGI underscores the importance of oncogene expression to growth regulation and evidences a positive correlation between cell growth and expression of c-fos, c-myc and c-ras. Furthermore, the effect of MDGI on expression of these genes indicates that it is a positive effector of cellular protooncogene expression, either directly or through one or more signaling pathways, or both.

It also has been shown that MDGI can function as a potent tumor suppressor gene. Human breast cancer cells transfected with a MDGI expression construct exhibited differentiated morphology, reduced proliferation rate, reduced clonogenicity in soft agar, and reduced tumorgenicity in nude mice. The human homologue of this gene was mapped to chromosome 1p33–35, a locus previously shown to exhibit frequent loss of heterozygosity in human breast cancer (about 40% of tumors). The magnitude of the in vivo and in vitro tumor suppressor activity of MDGI is comparable to that previously observed for BRCA1, p53, Rb, and H19.

The effects of MDGI on cell growth and differentiation, and on expression of cellular protooncogene expression reiterate the importance of soluble factors in normal growth and differentiation of cells, tissues, glands and organs, and their roles in aberrant cell growth, dysfunction and disease. Clearly, there is a need for factors that regulate growth and differentiation of normal and abnormal cells. There is a need, therefore, for identification and characterization of such factors that modulate growth and differentiation of cells, both normally and in disease states. In particular, there is a need to isolate and characterize additional cytostatins that modulate growth and differentiation of cells such as epithelial cells, particularly mammary epithelial cells, that are essential to the proper development and health of tissue and organs such as mammary glands of developing and adult human females.

SUMMARY OF THE INVENTION

Toward these ends, and others, it is an object of the present invention to provide polypeptides, inter alia, that have been identified as novel cytostatins by homology to known cytostatins, such as MDGI, of the amino acid sequence set out in FIG. 1 (SEQ ID NO:2).

It is a further object of the invention, moreover, to provide polynucleotides that encode cytostatins, particularly polynucleotides that encode the polypeptide herein designated cytostatin II.

In a particularly preferred embodiment of this aspect of the invention the polynucleotide comprises the region encoding human cytostatin II in the sequence set out in FIG. 1 (SEQ ID NO:1) or in the cDNA in ATCC deposit No. 97287 (referred to herein as the deposited clone).

In accordance with this aspect of the invention there are provided isolated nucleic acid molecules encoding human cytostatin II, including mRNAs, DNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of human cytostatin II.

It also is an object of the invention to provide cytostatin II polypeptides, particularly human cytostatin II polypeptides, that modulate growth activity of epithelial cells.

In accordance with this aspect of the invention there are provided novel polypeptides of human origin referred to herein as cytostatin II as well as biologically, diagnostically or therapeutically useful fragments, variants, homologs, analogs, and derivatives thereof.

Among the particularly preferred embodiments of this aspect of the invention are variants of human cytostatin II encoded by naturally occurring alleles of the human cytostatin II gene.

It is another object of the invention to provide a process for producing the aforementioned polypeptides, polypeptide fragments variants, analogs, derivatives and fragments thereof.

In a preferred embodiment of this aspect of the invention there are provided methods for producing the aforementioned cytostatin II polypeptides comprising culturing host cells having expressibly incorporated therein an exogenously-derived human cytostatin II-encoding polynucleotide under conditions for expression of human cytostatin II in the host and then recovering the expressed polypeptide.

It is another object of the invention to provide products, compositions, processes and methods for utilizing the aforementioned polypeptides and polynucleotides for biological, clinical and therapeutic purposes, inter alia.

In accordance with certain preferred embodiments of this aspect of the invention, there are provided methods for, among other things: modulating cell growth in vitro, ex vivo or in vivo; assessing cytostatin II expression in cells by determining protein or mRNA; and assaying genetic variation and aberrations, such as defects, in cytostatin II genes.

In accordance with certain preferred embodiments of this and other aspects of the invention there are provided probes that hybridize specifically to human cytostatin II sequences.

In certain additional preferred embodiments of this aspect of the invention there are provided antibodies against cytostatin II polypeptides. In certain particularly preferred embodiments in this regard, the antibodies are highly selective for human cytostatin II.

In accordance with another aspect of the present invention, there are provided cytostatin II agonists, such as those which mimic cytostatin II, bind to cytostatin II receptors and elicit cytostatin II-induced responses. Also among such agonists are those which interact with cytostatin II, or with other modulators or receptors, and thereby potentiate the effects of human cytostatin II.

In accordance with yet another aspect of the present invention, there are provided cytostatin II antagonists, such as those which mimic cytostatin II, bind to cytostatin II receptors but do not elicit cytostatin II-induced responses, and those that bind to or interact with human cytostatin II so as to inhibit its effects.

The agonists and antagonists may be used to mimic, augment or inhibit the action of such polypeptides, for example, and they may be used in the treatment of disorders associated with aberrant growth of cells affected by cytostatins, particularly cytostatin II.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide (SEQ ID NO:1) and deduced amino acid sequence (SEQ ID NO:2) of human cytostatin II.

GLOSSARY

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan. For analytical purposes, typically 1 $\mu$g of plasmid or DNA fragment is digested with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a proportionately larger volume. Appropriate buffers and substrate amounts for particular restriction enzymes are described in standard laboratory manuals, such as those referenced below, and they are specified by commercial suppliers. Incubation times of about 1 hour at 37° C. are ordinarily used, but conditions may vary in accordance with standard procedures, the supplier's instructions and the particulars of the reaction. After digestion, reactions may be electrophoresed directly on a polyacrylamide gel for analysis or to isolate a desired fragment or for both purposes.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region that regulates expression. Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means that the material has been altered from its natural state; e.g., that, if it occurs in nature, it has been removed from its original environment. For example, a naturally occurring polynucleotide or a polypeptide naturally present in a living animal in its natural state is not "isolated," but the same polynucleotide or polypeptide separated from some or all of the coexisting materials in the natural system is "isolated", as the term is employed herein.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, $2^{ND}$ Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides. Most often the term refers to single-stranded deoxyribonucleotides, but it can refer as well to short single-or double-stranded ribonucleotides, short RNA:DNA hybrids and short double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' ends of chemically synthesized oligonucleotides generally have a free hydroxyl group and, in the presence of a ligase, such as T4 DNA ligase, readily form phosphodiester bonds with the 5' phosphate of other polynucleotides. As is well known, this reaction can be prevented, where desired, by 5' dephosphorylation of other polynucleotides in a reaction.

PLASMIDS generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

DESCRIPTION OF THE INVENTION

The present invention relates to novel cytostatin II polypeptides and polynucleotides, among other things, as described in greater detail below. In particular, the invention relates to polypeptides and polynucleotides of a novel human cytostatin II, which is related by amino acid sequence homology to the mammary derived growth inhibitor ("MDGF") found in cows and mice. The invention relates especially to cytostatin II polynucleotide and amino acid sequences set out in FIG. 1 (SEQ ID NO:1 AND 2).
Polynucleotides The present invention relates to novel cytostatin II polypeptides and polynucleotides, among other things, as described in greater detail below. In particular, the invention relates to polypeptides and polynucleotides of a novel human cytostatin II, which is related by amino acid sequence homology to the mammary derived growth inhibitor ("MDGI ") found in cows and mice. The invention relates especially to cytostatin II polynucleotide and amino acid sequences set out in FIG. 1 (SEQ ID NO:1 AND 2).

Using the information provided herein, such as the polynucleotide sequence set out in FIG. 1 (SEQ ID NO:1), a polynucleotide of the present invention encoding human cytostatin II polypeptide may be obtained using standard cloning and screening procedures, such as those for cloning cDNAs using mRNA of epithelial cells as starting material.

Illustrative of the invention, the polynucleotide set out in FIG. 1 (SEQ ID NO:1) was discovered in a cDNA library derived from mRNA of human fetal brain tissue.

Human cytostatin II of the invention is structurally related to other proteins of the cytostatin family of growth modulating factors, as shown by the results of sequencing the cDNA encoding human cytostatin II in ATCC Deposit No. 97287. This cDNA sequence, set out in FIG. 1 (SEQ ID NO:1), contains an open reading frame encoding a protein of about 132 amino acid residues with a deduced molecular weight of about 14.8 kDa. The protein exhibits a high degree of homology to mouse mammary-derived growth inhibitor (also called "MDGI"), with which it shares 64% identity and 79% similarity over a 132 amino acid stretch.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded, and if single stranded may be the coding strand or non-coding (anti-sense) strand. The polynucleotides may have naturally occurring sequences, such as those of naturally occurring allelic variants, or they may have sequences that have been altered, for instance, by in vitro mutagenesis techniques.

The coding sequence which encodes the polypeptide may be identical to the coding sequence of the polynucleotide shown in FIG. 1 (SEQ ID NO:1) or that of the deposited clone. It also may be a polynucleotide with a different sequence, which, as a result of the redundancy (degeneracy) of the genetic code, encodes the polypeptide of the DNA of FIG. 1 (SEQ ID NO:1) or of the deposited cDNA.

Polynucleotides of the present invention which encode the polypeptide of FIG. 1 (SEQ ID NO:2) or the polypeptide encoded by the deposited cDNA may include, but are not limited to the coding sequence for the mature polypeptide, by itself; the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA.

In accordance with the foregoing, the term "polynucleotide encoding a polypeptide" as used herein encompasses polynucleotides which include a sequence encoding a polypeptide of the present invention, particularly the human cytostatin II having the amino acid sequence set out in FIG. 1 (SEQ ID NO:2) or the amino acid sequence of the human cytostatin II encoded by the cDNA in 97287. The term encompasses polynucleotides that include a single continuous region or discontinuous regions encoding the polypeptide, together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1 (SEQ ID NO:2) or the polypeptide encoded by the cDNA of the deposited clone. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

The present invention includes polynucleotides encoding the same mature polypeptide as shown in FIG. 1 (SEQ ID NO:2) or the same mature polypeptide encoded by the cDNA of the deposited clone. Further, the invention includes variants of such polynucleotides that encode a fragment, derivative or analog of the polypeptide of FIG. 1 (SEQ ID NO:2) or the polypeptide encoded by the cDNA of the deposited clone. Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Variants of the invention may have a sequence that occurs in nature or they may have a sequence that does not occur naturally. As herein above indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides.

Among the particularly preferred embodiments of the invention in this regard are polynucleotides encoding polypeptides having the amino acid sequence of cytostatin II set out in FIG. 1 (SEQ ID NO:2) or the amino acid sequence of cytostatin II of the cDNA of the deposited clone; variants, analogs, derivatives and fragments thereof, and fragments of the variants, analogs and derviatives Further particularly preferred in this regard are polynucleotides encoding cytostatin II variants, analogs, derivatives and fragments, and variants, analogs and derivatives of the fragments, which have the amino acid sequence of the cytostatin II polypeptide of FIG. 1 (SEQ ID NO:2) or of the deposit in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the cytostatin II. Also especially preferred in this regard are conservative substitutions. Most highly preferred are polypeptides having the amino acid sequence of FIG. 1 (SEQ ID NO:2) or of the deposit, without substitutions.

Further preferred embodiments of the invention are polynucleotides that are more than 85% identical to a polynucleotide encoding the cytostatin II polypeptide having the amino acid sequence set out in FIG. 1 (SEQ ID NO:2), or variants, close homologs, derivatives and analogs thereof, as described above. Alternatively, most highly preferred are polynucleotides that comprise a region that is more than 85% identical to a polynucleotide encoding the cytostatin II polypeptide of the cDNA of the deposited clone. In this regard, polynucleotides more than 90% identical to the same are particularly preferred, and among these particularly preferred polynucleotides, those with 95% or more identity are especially preferred. Furthermore, those with 97% or more identity are highly preferred among those with 95% or more identity, and among these those with 98% or more and 99% or more identity are particularly highly preferred, with 99% or more being the more preferred.

Also particularly preferred in this regard are polynucleotides encoding a polypeptide having the amino acid sequence of the cytostatin set out in FIG. 1 (SEQ ID NO:2) or of the deposited clone. As set out elsewhere herein, the polynucleotide may encode the polypeptide in a continuous region or in a plurality of two or more discontinuous exons, and it may comprise additional regions as well, which are unrelated to the coding region or regions.

Most highly preferred in this regard are polynucleotides that comprise a region that is more than 85% identical to the cytostatin II-encoding portion of the polynucleotide set out in FIG. 1 (SEQ ID NO:1). Alternatively, most highly preferred are polynucleotides that comprise a region that is more than 85% identical to the cytostatin II-encoding portion of the cDNA the deposited clone. Among such polynucleotides, those more than 90% identical to the same are particularly preferred, and, among these particularly preferred polynucleotides, those with 95% or more identity are especially preferred. Furthermore, those with 97% or more identity are highly preferred among those with 95% or more identity, and among these those with 98% or more and 99% or more identity are particularly highly preferred, with 99% or more being the more preferred of these.

The present invention also includes polynucleotides in which the sequence encoding the mature polypeptide is fused in the same reading frame to additional sequences. Such sequences include signal sequences, which facilitate transport of the nascent protein into the endoplasmic reticulum, pro-sequences that are associated with inactive precursor forms of the poiypeptide, which may facilitate trafficking of the protein in a cell or out of a cell or may improve persistence of the protein in a cell or in an extracellular compartment. Such sequences also may be added to facilitate production and purification, or to add additional functional domains, as discussed elsewhere herein.

Thus, polynucleotides of the invention may encode, in addition to a mature cytostatin, particularly cytostatin II, for example, a leader sequence, such as a signal peptide which functions as a secretory sequence for controlling transport of the polypeptide into the lumen of the endoplasmic reticulum. The leader sequence may be removed by the host cell, as is generally the case for signal peptides, yielding another precursor protein or the mature polypeptide. A precursor protein having a leader sequence often is called a preprotein.

The polynucleotides also may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

A polynucleotide of the present invention may encode a mature or precursor pre-, pro- or prepropolypeptide as discussed above, among others, fused to additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the vector pQE-9, among others, many of which are commercially available. As described in Gentz et al., *Proc. Natl. Acad. Sci., USA* 86: 821–824 (1989), for instance, hexa-histidine provides for convenient purification of the fusion protein. Typically, it does not adversely affect protein structure or function, and it binds efficiently, selectively and tightly to metal chelate resins, particularly nickel chelate resins. For instance, as is well known, hexa-histidine tags often bind especially well to nickel-NTA resin, which is well known and readily available and can be obtained commercially from, for instance, Qiagen. Moreover, the histidine-metal interaction not only is stable to a variety of conditions useful to remove non-specifically bound material, but also the fusion polypeptide can be bound and removed under mild, non-denaturing conditions. The hexa-histidine tag can be fused most conveniently to the amino or the carboxyl terminus of the cytostatin polypeptide. A tag of the hexa-histidine type is particularly useful for bacterial expression.

Another useful marker sequence in certain other preferred embodiments is a hemagglutinin ("HA") tag, particularly when a mammalian cell is used for expression; e.g., COS-7 cells. The HA tag corresponds to an epitope derived of influenza hemagglutinin protein, which has been described by Wilson et al., *Cell* 37: 767 (1984), for instance.

Probes

The present invention further relates to polynucleotides that hybridize to the herein above-described cytostatin sequences, particularly cytostatin 2 sequences. Preferred in this regard are polynucleotides that have at least 50% identity to the sequences described herein above. Particularly preferred are sequences that have at least 70% identity. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Particularly preferred embodiments in this respect, moreover, are polynucleotides which hybridize to the above-described polynucleotides and encode polypeptides which retain substantially the same biological function or activity as the mature polypeptide encoded by the cDNA of FIG. 1 (SEQ ID NO:1) or the cDNA of the deposited clone.

Deposited Materials

A deposit containing a human cytostatin II cDNA has been deposited with the American Type Culture Collection ("ATCC"), 10801 University Boulevard, Manassas, Va. 20110–2209. The deposit, which has been given accession number 97287, is referred to herein as "the deposited clone."

The deposit will be maintained under the terms of the Budapest Treaty on the International Recognition of the Deposit of Micro-organisms for purposes of Patent Procedure.

These deposit is provided merely as convenience to those of skill in the art and it is not an indication or an admission that a deposit is required for enablement, such as that required under 35 U.S.C. §112.

The sequence of the polynucleotides contained in the deposited materials, as well as the amino acid sequence of the polypeptides encoded thereby, are incorporated herein by reference and are controlling in the event of any conflict with any description of sequences herein.

A license may be required to make, use or sell the deposited materials, and no such license is hereby granted.

Polypeptides

The present invention further relates to a human cytostatin II polypeptide which has the deduced amino acid sequence of FIG. 1 (SEQ ID NO:2) or which has the amino acid sequence encoded by the deposited clone.

The invention also relates to fragments, analogs and derivatives of these polypeptides. The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 (SEQ ID NO:2) or that encoded by the cDNA in the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of cytostatin II set out in FIG. 1 (SEQ ID NO:2), variants, analogs, derivatives and fragments thereof, and variants, analogs and derivatives of the fragments. Alternatively, particularly preferred embodiments of the invention in this regard are polypeptides having the amino acid sequence of the cytostatin II of the cDNA in the deposited clone, variants, analogs, derivatives and fragments thereof, and variants, analogs and derivatives of the fragments.

Further particularly preferred in this regard are variants, analogs, derivatives and fragments, and variants, analogs and derivatives of the fragments, having the amino acid sequence of the cytostatin II polypeptide of FIG. 1 (SEQ ID NO:2) or of the cDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the cytostatin II. Also especially preferred in this regard are conservative substitutions. Most highly preferred are polypeptides having the amino acid sequence of FIG. 1 (SEQ ID NO:2) or the deposited clone without substitutions.

The polypeptides and polynucleotides of the present invention are preferably provided in an isolated form, and preferably are purified to homogeneity.

The term "isolated" means that the material has been altered from its natural state; e.g., that, if it occurs in nature, it has been removed from its original environment. For example, a naturally occurring polynucleotide or polypeptide naturally present in a living animal in its natural state is not "isolated," but the same polynucleotide or polypeptide separated from some or all of the coexisting materials in the natural system is "isolated", as the term is employed herein.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or enviromnent. Similarly, the polynucleotides and polypeptides may occur in a composition, such as a media formulation, a solution for introduction into cells, a composition or solution for chemical or enzymatic reaction, and the like, which are not naturally compositions, and therein remain isolated polynucleotides or polypeptides within the meaning of that term as it is employed herein.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited elsewhere herein, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papovaviruses such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda $P_L$ promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS, pD10, phagescript, psiX174, pbluescript SK, pbsks, pNH8A, pNH 16a, pNH18A, pNH46A, available from Stratagene; and ptrc99a, pKK223-3, pKK233-3, pDR540, pRIT5 available From Pharmacia. Among preferred eukaryotic vectors are pWLNEO, pSV2CAT, pOG44. pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ and promoters, the T3 and T7 promoters, the gpt promoter, the lambda $P_R$, $P_L$ promoters and the trp promoter.

Among known eukaryotic promoters suitable in this regard are the CMV immediate early promoter, the HSV thymidine kinase promoter, the early and late SV40 promoters, the promoters of retroviral LTRs, and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trpl gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include Escherichia coli, Bacillus subtilis and Salmonella typhimurium. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include. for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman, Cell 23: 175 (1981). Other cell lines capable of expressing a compatible vector include for example, the C127, 3T3, CHO, HeLa and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The cytostatin II polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") also can be employed especially for final purification steps. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Further Illustrative Applications

Cytostatin II polynucleotides and polypeptides may be used in accordance with the present invention for a variety of applications, particularly those that make use of the chemical and biological properties cytostatin II. Among these are applications in characterizing cells and organisms and in growing cells and organisms. Additional applications relate to diagnosis or treatment or disorders of cells, tissues and organisms.

Thus, among others, the growth inhibitory and differentiation stimulating activity of cytostatin II is useful to inhibit growth and stimulate differentiation of tumor cells, such as tumor cell in vitro, as for biological purposes. The same activities may be applied to treatment of aberrant cell growth in an organism, such as cells of a tumor. In these regards, cytostatin II polypeptides are preferred, particularly the cytostatin II having the amino acid sequence set out in FIG. 1 (SEQ ID NO:2) or the amino acid sequence of the cytostatin II of the cDNA of the deposited clone.

Similarly, the ability of cytostatin II to inhibit growth of endothelial cells, such as venous endothelial cells may be used to prevent, slow or alter angiogenesis in culture or in situ.

In a related vein, since tumor cells at sites of metastasis, as well as those at an original site, must attract new blood vessels to grow, cytostatin II inhibition of venous endothelial cells may be useful to reduce metastatic potential or to slow progression of metastatic disease.

Furthermore, activity of cytostatin II that inhibits mammary epithelial cell growth and modulation mammary gland differentiation also may be used to promote formation of alveolar buds, aid development of differentiated lobuloalveoli, and stimulate the production of milk protein and the accumulation of fat droplets. Such lactation-stimulating activity may aid milk production in commercial milk-producing mammals and it may be useful to aid milk-production by human mothers, for instance.

In a related application, modulating activity of cytostatin II that affects breast size may be useful to aid return of an enlarged breast to normal size after parturition.

Inhibition of cytostatin II activity, for instance, by antisense phosphorothioates or by antibodies, may be useful for selective inhibition of endogenous cytostatin II activity in mammary epithelial cells to suppress the appearance of alveolar end buds and to lower the beta-casein level.

As set out further below, these and other activities and properties of the cytostatin II polynucleotides and polypeptides of the invention have various applications and uses in numerous fields including applications involving growth of cells in vitro, commercial production of milk and milk products, and diagnosis and treatments relating to the fields of oncology, cardiology, immunology, endocrinology, hematology, metabolic disorders, musculoskelatal problems and gynecology and obstetrics, to name a few.

The full length cytostatin II cDNA in whole or part may be used as a hybridization probe for cDNA and genomic DNA to isolate full-length cDNAs and genomic clones encoding cytostatin II and to isolate cDNA and genomic clones of other genes that have a high sequence similarity to the human cytostatin II gene. Such probes generally have at least 20 bases. Preferably, however, the probes have at least 30 bases and do not exceed 50 bases.

Such probes may also be used to identify additional cDNA clones corresponding to a full length transcript and a genomic clone or clones that contain the complete human cytostatin II gene including regulatory and promoter regions, exons, and introns.

For example, the coding region of the cytostatin II gene may be isolated by screening using the known DNA sequence to synthesize an oligonucleotide probe. Labeled an oligonucleotide having a sequence complementary to that of a gene of the present invention then is used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease.

Cytostatin II-binding Molecules

This invention also provides a method for identification of molecules, such as receptor molecules, that bind cytostatin II. Genes encoding proteins that bind cytostatin II, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to cytostatin II, a cDNA library is created from this RNA, the library is divided into pools and the pools are transfected individually into cells that are not responsive to cytostatin II. The transfected cells then are exposed to labeled cytostatin II. (Cytostatin II can be labeled by a variety of well-known techniques including standard methods of radio-iodination or inclusion of a recognition site for a site-specific protein kinase.) Following exposure, the cells are fixed and binding of cytostatin is determined. These procedures conveniently are carried out on glass slides.

Pools are identified of cDNA that produced cytostatin II-binding cells. Sub-pools are prepared from these positives, transfected into host cells and screened as described above. Using an iterative sub-pooling and re-screening process, one or more single clones that encode the putative binding molecular, such as a receptor, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor.

Polypeptides of the invention also can be used to assess cytostatin II binding capacity of cytostatin II binding molecules, such as receptors,. in cells or in cell-free preparations.

Agonists and Antagonists and Assays Therefor

The invention also provides a method of screening compounds to identify those which enhance or block the action of cytostatin II on cells, such as its interaction with cytostatin II-binding molecules such as receptors. An agonist is a compound which increases the natural biological functions of cytostatin II, while antagonists decrease or eliminate such functions.

For example, a cellular compartment, such as a membrane or a preparation thereof, such as a membrane-preparation, may be prepared from a cell that expresses a molecule that binds cytostatin II, such as a molecule of a signaling or regulatory pathway modulated by cytostatin II. The preparation is incubated with labeled cytostatin II in the absence or the presence of a candidate molecule which may be a cytostatin II agonist or antagonist. The ability of the candidate molecule to bind the binding molecule is reflected in decreased binding of the labeled ligand. Molecules which bind gratuitously, i.e., without inducing the effects of cytostatin II on binding the cytostatin II binding molecule, are most likely to be good antagonists. Molecules that bind well and elicit effects that are the same as or closely Cytostatin II-like effects of potential agonists and antagonists may by measured, for instance, by determining activity of a second messenger system following interaction of the candidate molecule with a cell or appropriate cell preparation, and comparing the effect with that of cytostatin II or molecules that elicit the same effects as cytostatin II. Second messenger systems that may be useful in this regard include but are not limited to AMP guanylate cyclase, ion channel or phosphoinositide hydrolysis second messenger systems.

Another example of an assay for cytostatin II antagonists is a competitive assay that combines cytostatin II and a potential antagonist with membrane-bound cytostatin II receptors or recombinant cytostatin II receptors under appropriate conditions for a competitive inhibition assay. Cytostatin II can be labeled, such as by radioactivity, such that the number of cytostatin II molecules bound to receptor can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor, without inducing cytostatin II-induced activities, thereby preventing the action of cytostatin II by excluding cytostatin II from binding.

Potential antagonists include a small molecule which binds to and occupies the binding site of the polypeptide thereby preventing binding to cellular binding molecules, such as receptors, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, *J. Neurochem.* 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan etal., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of cytostatin II. The antisense RNA oligonucleotide hybridizes to the mRNA in vivo and blocks translation of the mRNA molecule into cytostatin II polypeptide. The oligonucleotides described above can also be delivered to cells such that the antisense RNA or DNA may be expressed in vivo to inhibit production of cytostatin II.

The antagonists may be employed in a composition with a pharmaceutically acceptable carrier, e.g., as hereinafter described.

The antagonists may be employed for instance to treat cardiac myocte hypertrophy or leukemia.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The cytostatin II polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques* 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, ΨCRE, ΨCRIP, GP+E-86, GP+envAm12, and DAN cell lines as described in Miller, A., *Human Gene Therapy* 1: 5–14 (1990). The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are riot limited to, embryonic stem cells, embryonic carcinoma cells, as well as hematopoietic stem cells, hepatocytes, fibroblasts, myoblasts, keratinocytes, endothelial cells, and bronchial epithelial cells.

Polynucleotide Assays

This invention is also related to the use of the cytostatin II polynucleotides to detect complementary polynucleotides such as, for example, as a diagnostic reagent. Detection of a mutated form of cytostatin II associated with a dysfunction will provide a diagnostic tool that can add or define a diagnosis of a disease or susceptibility to a disease which results from under-expression over-expression or altered expression of cytostatin II, such as, for example, breast cancer.

Individuals carrying mutations in the human cytostatin II gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature*, 324: 163–166 (1986)) prior to analysis. RNA or CDNA may also be used in the same ways. As an example, PCR primers complementary to the nucleic acid encoding cytostatin II can be used to identify and analyze cytostatin II expression and mutations. For example, deletions and insertions can be detected by a change in size of the amplified product in comparison to the normal genotype. Point mutations can be identified by hybridizing amplified DNA to radiolabeled cytostatin II RNA or alternatively, radiolabeled cytostatin II antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science*, 230: 1242 (1985)).

Sequence changes at specific locations also may be revealed by nuclease protection assays, such as RNase and S1 protection or the chemical cleavage method (e.g., Cotton et al., *Proc. Natl. Acad. Sci., USA*, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Polypeptide Assays

The present invention also relates to a diagnostic assays such as quantitative and diagnostic assays for detecting levels of cytostatin II protein in cells and tissues, including determination of normal and abnormal levels. Thus, for instance, a diagnostic assay in accordance with the invention for detecting over-expression of cytostatin II protein compared to normal control tissue samples may be used to detect the presence of myocardial infarction, for example. Assay techniques that can be used to determine levels of a protein, such as an cytostatin II protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to cytostatin II, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any cytostatin II proteins attached to the polystyrene dish. Unbound monoclonal antibody is washed out with buffer. The reporter antibody linked to horseradish peroxidase is placed in the dish resulting in binding of the reporter antibody to any monoclonal antibody bound to cytostatin II. Unattached reporter antibody is then washed out. Reagents for peroxidase activity, including a calorimetric substrate are then added to the dish. Immobilized peroxidase, linked to cytostatin II through the primary and secondary antibodies, produces a colored reaction product. The amount of color developed in a given time period indicates the amount of cytostatin II protein present in the sample. Quantitative results typically are obtained by reference to a standard curve.

A competition assay may be employed wherein antibodies specific to cytostatin II attached to a solid support and labeled cytostatin II and a sample derived from the host are passed over the solid support and the amount of label detected attached to the solid support can be correlated to a quantity of cytostatin II in the sample.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the express sequence tag (EST) was derived, and the longer the better. For example, 2,000 bp is good, 4,000 is better, and more than 4,000 is probably not necessary to get good results a reasonable percentage of the time. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Immunological Applications

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature* 256: 495–497 (1975), the trioma technique, the human B-cell hybridoma technique (Kozbor et al., *Immunology Today* 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All parts or amounts set out in the following examples are by weight, unless otherwise specified.

Unless otherwise stated size separation of fragments in the examples below was carried out using standard techniques of polyacrylamide gel electrophoresis ("PAGE") in 8 percent gels, as described, for instance, by Goeddel et al., *Nucleic Acids Res.* 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 µg of DNA.

All examples were carried out using standard techniques, which are well known and routine to those of skill in the art, except where otherwise described in detail.

Example 1
Expression and Purification of Human Cytostatin II Using Bacteria

The DNA sequence encoding human cytostatin II in the deposited polynucleotide was amplified using PCR oligonucleotide primers specific to the amino acid carboxyl terminal sequence of the human cytostatin II protein and to vector sequences 3' to the gene. Additional nucleotides containing restriction sites to facilitate cloning were added to the 5' and 3' sequences respectively.

The 5' oligonucleotide primer had the sequence 5' CGC GGA TCC GTG GAG GCT TTC TG 3' (SEQ ID NO: 3) containing the underlined BamH1 restriction site followed by 14 nucleotides of human cytostatin II coding sequence starting from the second codon; i.e., the codon following the AUG for the presumptive N-terminal methionine.

The 3' primer had the sequence 5' CGC AAG CTT TTA TGC CTT CTC ATA GTG 3' (SEQ ID NO:4) containing the underlined Hind III restriction site followed by 18 nucleotides complementary to the last 6 codons of cytostatin II including the stop codon.

The restrictions sites were convenient to restriction enzyme sites in the bacterial expression vectors pQE-70, which were used for bacterial expression in these examples. (Qiagen, Inc. 9259 Eton Avenue, Chatsworth, Calif., 91311). pQE-70 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

pQE-70 was digested with BamH1 and HindIII and amplified human cytostatin II DNA was ligated into the BamH1/HindIII digested vector DNA. The insertion into the BamH1/HindIII restricted vector placed the cytostatin II coding region downstream of the IPTG-inducible promoter and in-frame with an initiating AUG for translation.

The ligation mixture was transformed into competent *E. coli* cells using standard procedures. Such procedures are described in Sambrook et al., MOLECULAR CLONING: A LABORATORY MANUAL, $2^{ND}$ Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan$^r$"), was used in carrying out the illustrative example described here. This strain, which is only one of many that are suitable for expressing cytostatin II, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/ml) and kanamycin (25 ug/ml).

The O/N culture was used to inoculate a large culture, at a dilution of approximately 1:100 to 1:250. The cells were grown to an optical density at 600 hm (O.D.$^{600}$) of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea was exchanged into 2xphosphate buffered saline ("PBS") and protein was then refolded in standard PD-10 solution. The protein was further purified by size exclusion chromatography and then by a further step of chromatography to remove endotoxin. The sterile filtered protein preparation was stored in 2xPBS at a concentration of 95 micrograms per mL.

Analysis of the preparation by standard methods of polyacrylamide gel electrophoresis revealed that the preparation contained about 80% monomer cytostatin II having the expected molecular weight of, approximately, 14 kDa.

Example 2
Cloning and Expression of Human Cytostatin II in a Baculovirus Expression System The cDNA sequence encoding the full length human cytostatin II protein, in the deposited clone is amplified using PCR oligonucleotide primers corresponding to the 5' and 3' sequences of the gene:

The 5' primer has the sequence GC GGA TCC CGT GGA GGC TTT CTG TGC (SEQ ID NO:5) containing the underlined BamH1 restriction enzyme site followed by codons 2–5 and 2 bases of codon 6 of the sequence of cytostatin II of FIG. 1 (SEQ ID NO:1). Inserted into an expression vector, as described below, the 5' end of the amplified fragment encoding human cytostatin II provides an efficient signal for the initiation of translation in eukaryotic cells, as described by Kozak, M., *J. Mol. Biol.*, 196: 947–950 (1987), among others.

The 3' primer has the sequence 5' GC GGT ACC TTA TGC CTT CTC ATA GTG' 3' (SEQ ID NO:8) containing the underlined Asp718 restriction followed by nucleotides complementary to the stop codon and the codons for the last five amino acids of the human cytostatin II cDNA of FIG. 1 (SEQ ID NO:1).

The amplified fragment is isolated from a 1% agarose gel using a commercially available kit ("Geneclean," BIO 101 Inc., La Jolla, Calif.). The fragment then is digested with BamH1 and Asp718 and again is purified on a 1% agarose gel. This fragment is designated herein F2.

The vector pA2-GP is used to express the cytostatin II protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamH1 site. The polyadenylation site of the simian virus 40 ("SV40") is used for efficient polyadenylation. For an easy selection of recombinant virus the beta-galactosidase gene from *E.coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1. Such vectors are described in Luckow et al., *Virology* 170: 31–39, among others.

The plasmid is digested with the restriction enzymes BamH1 and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 were ligated together with T4 DNA ligase. *E.coli* HB101 cells were transformed with ligation mix and spread on culture plates. Bacteria were identified that contained the plasmid with the human cytostatin II gene by digesting DNA from individual colonies using BamH1 and Asp718 and then analyzing the digestion product by gel electrophoresis. The sequence of the cloned fragment was confirmed by DNA sequencing. This plasmid is designated herein pBacCytostatin II.

5 μg of the plasmid pBacCytostatin II was co-transfected with 1.0 μg of a commercially available linearized baculovirus DNA ("BaculoGold™ baculovirus DNA", Pharmingen, San Diego, Calif.), using the lipofection method described by Felgner et al.; *Proc. Natl. Acad. Sci. USA* 84: 7413–7417 (1987). 1 μg of BaculoGold™ virus DNA and 5 μg of the plasmid pBacCytostatin II are mixed in a sterile well of a microtiter plate containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith (supra). An agarose gel with "Blue Gal" (Life Technologies Inc., Gaithersburg) is used to allow easy identification and isolation of gal-expression clone, which produce blue-stained plaques. (A detailed description of a "plaque assay" of this type can also be found in the user's guide for insect cell culture and baculovirology distributed by Life Technologies Inc., Gaithersburg, page 9–10).

Four days after the serial dilution the virus is added to the cells. Blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted cytostatin II is identified by DNA analysis including restriction mapping and sequencing. This is designated herein as V-cytostatin II.

Sf9 cells are grown in Grace's medium supplemented with 10% heat-inactivated FBS. The cells are infected with the recombinant baculovirus V-Cytostatin II at a multiplicity of infection ("MOI") of 2. Six hours later the medium is removed and is replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours and they are then harvested by centrifugation, lysed and the labeled proteins were visualized by SDS-PAGE and autoradiography.

Example 3

Expression of Human Cytostatin II in COS Cells

The expression plasmid, Cytostatin II HA, is derived from the vector pcDNAI/Amp (Invitrogen) containing: 1) SV40 origin of replication, 2) ampicillin resistance gene, 3) *E.coli* replication origin, 4) CMV promoter followed by a polylinker region, an SV40 intron and polyadenylation site. A DNA fragment encoding the entire Cytostatin II precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA epitope.

The plasmid construction strategy is as follows.

The DNA sequence encoding cytostatin II of the deposited clone was constructed by PCR on the original EST cloned using two primers. The 5' primer is GCGC GGATCC GCC ACC ATG GTG GAG GCT TTC TGT, (SEQ ID NO:6) containing the underlined BamH1 site followed by 8 nucleotides of cytostatin II coding sequence starting from the initiation codon. The 3' sequence is GCGC TCTAGA TCA AGC GTA GTC TGG GAC GTC GTA TGG GTA TGC CTT ATA GTG (SEQ ID NO:7) containing the underlined XbaI site, a translation stop codon, an HA tag and the last 12 nucleotides of the cytostatin II coding sequence (not including the stop codon).

Therefore, the PCR product contains a BamH1 site, the cytostatin II coding sequence followed by HA tag fused to cytostatin II in frame, a translation termination stop codon next to the HA tag, and an XbaI site.

The PCR amplified DNA fragment and the vector, pcDNAI/Amp, are digested with BamH1 and XbaI and then ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment.

For expression of recombinant cytostatin II, COS cells are transfected with the expression vector using methods described in, for example DEAE-DEXTRAN, as described for instance in Sambrook et al., MOLECULAR CLONING: A LABORATORY MANUAL, Cold Spring Laboratory Press, Cold Spring Harbor, N.Y. (1989). The expression of the cytostatin II HA fusion protein is detected by radiolabelling and immunoprecipitation, using methods described in, for example Harlow et al., ANTIBODIES: A LABORATORY MANUAL, $2^{ND}$ Ed.; Laboratory Press, Cold Spring Harbor, N.Y. (1988). Cells are labeled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson et al., Id.). Both cell lysate and culture media are precipitated with an HA specific monoclonal antibody. Proteins precipitated are analyzed on 15% SDS-PAGE gels, which shows an expression product of the expected size.

Example 4
Tissue Distribution of Cytostatin II Expression

Northern blot analysis is carried out to examine the levels of expression of cytostatin II in human tissues, using methods described by, among others, Sambrook et al, cited above. Total cellular RNA samples are isolated with RNAzol™ B system (Biotecx Laboratories, Inc. 6023 South Loop East, Houston, Tex. 77033). About 10 μg of total RNA isolated from each human tissue specified is separated on a 1% agarose gel. The gel is blotted onto a nylon filter full-length cytostatin II gene and hybridized to a labeled polynucleotide probe. The labeling reaction is done according to the Stratagene Prime-It kit with 50 ng DNA fragment. The labeled DNA is purified with a Select-G-50 column (5 Prime-3 Prime, Inc. 5603 Arapahoe Road, Boulder, Colo. 80303). The filter is then hybridized with the radioactive labeled full length cytostatin II gene at 1,000,000 cpm/ml in 0.5 M $NaPO_4$, pH 7.4 and 7% SDS overnight at 65° C. After washing twice at room temperature and twice at 60° C. with 0.5×SSC, 0.1% SDS, the filter is dried and then exposed to film at −70° C. overnight with an intensifying screen. The mRNA for cytostatin II is abundant in brain.

Example 5
Gene Therapeutic Expression of Human Cytostatin II

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

Cytostatin cDNA capable of expressing active cytostatin II, is isolated. The ends of the fragment are modified, if necessary, for cloning into the vector. For instance, 5" overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the cytostatin II fragment are mixed together and joined using T4 DNA ligase. The ligation mixture is used to transform E. Coli and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the cytostatin II gene is introduced into the packaging cells by standard techniques. Infectious viral particles containing the cytostatin II gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce cytostatin II product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated protein comprising a polypeptide having an amino acid sequence of amino acids 1 to 132 of SEQ ID NO:2.

2. The isolated protein of claim 1, wherein the polypeptide further comprises a heterologous polypeptide sequence.

3. The isolated protein of claim 2, wherein the heterologous polypeptide sequence is the Fc domain of an immunoglobulin.

4. The isolated protein of claim 1, wherein said protein is pegylated.

5. A composition comprising the protein of claim 1 and a pharmaceutically acceptable carrier.

6. An isolated protein of claim 1 produced by a method comprising:
  (a) synthesizing the protein of claim 1 in a cell; and
  (b) recovering the protein.

7. An isolated protein comprising a polypeptide having the amino acid sequence of the full-length polypeptide encoded by the cDNA contained in ATCC Deposit No. 97287.

8. The isolated protein of claim 7, wherein the polypeptide further comprises a heterologous polypeptide sequence.

9. The isolated protein of claim 8, wherein the heterologous polypeptide sequence is the Fc domain of an immunoglobulin.

10. The isolated protein of claim 7, wherein said protein is pegylated.

11. A composition comprising the protein of claim 7 and a pharmaceutically acceptable carrier.

12. An isolated protein of claim 7 produced by a method comprising:
  (a) synthesizing the protein of claim 7 in a cell; and
  (b) recovering the protein.

13. An isolated protein comprising a polypeptide having an amino acid sequence selected from the group consisting of:
  (a) a polypeptide of amino acids 1 to 132 as set forth in SEQ ID NO:2 which inhibits cellular growth, in which 1 to 5 amino acid residues are substituted, deleted or added in any combination; and
  (b) a polypeptide amino acids 1 to 132 as set forth in SEQ ID NQ:2 which inhibits cellular growth, in which 5 to 10 amino acid residues are substituted, deleted or added in any combination.

14. The isolated protein of claim 13, wherein said amino acid sequence is (a).

15. The isolated protein of claim 13, wherein said amino acid sequence is (b).

16. The isolated protein of claim 13, wherein the polypeptide further comprises a heterologous polypeptide sequence.

17. The isolated protein of claim 16, wherein the heterologous polypeptide sequence is the Fc domain of an immunoglobulin.

18. The isolated protein of claim 13, wherein said protein is pegylated.

19. A composition comprising the protein of claim 13 and a pharmaceutically acceptable carrier.

20. An isolated protein of claim 13 produced by a method comprising:
  (a) synthesizing the protein of claim 13 in a cell; and
  (b) recovering the protein.

21. An isolated protein comprising a polypeptide having an amino acid sequence selected from the group consisting of:
  (a) the amino acid sequence of the full-length polypeptide encoded by the cDNA contained in ATCC Deposit No. 97287 which inhibits cellular growth, in which 1 to 5 amino acid residues are substituted, deleted or added in any combination; and
  (b) the amino acid sequence of the full-length polypeptide encoded by the cDNA contained in ATCC Deposit No. 97287 which inhibits cellular growth, in which 5 to 10 amino acid residues are substituted, deleted or added in any combination.

22. The isolated protein of claim 21, wherein said amino acid sequence is (a).

23. The isolated protein of claim 21 wherein said amino acid sequence is (b).

24. The isolated protein of claim 21, wherein the polypeptide further comprises a heterologous polypeptide sequence.

25. The isolated protein of claim 24, wherein the heterologous polypeptide sequence is the Fc domain of an immunoglobulin.

26. The isolated protein of claim 21, wherein said protein is pegylated.

27. A composition comprising the protein of claim 21 and a pharmaceutically acceptable carrier.

28. An isolated protein of claim 21 produced by a method comprising:
  (a) synthesizing the protein of claim 21 in a cell; and
  (b) recovering the protein.

29. An isolated protein consisting of a fragment of at least 50 contiguous amino acid residues of SEQ ID NQ:2.

30. The isolated protein of claim 29, wherein the polypeptide further comprises a heterologous polypeptide sequence.

31. The isolated protein of claim 30, wherein the heterologous polypeptide sequence is the Fc domain of an immunoglobulin.

32. The isolated protein of claim 29, wherein said protein is pegylated.

33. A composition comprising the protein of claim 29, and a pharmaceutically acceptable carrier.

34. An isolated protein produced by a method comprising:
  (a) synthesizing the protein of claim 29 in cell; and
  (b) recovering the protein.

35. An isolated protein consisting of a fragment of at least 50 contiguous amino acid residues of the full-length polypeptide encoded by the cDNA contained in ATCC Deposit No. 97287.

36. The isolated protein of claim 35, wherein the polypeptide further comprises a heterologous polypeptide sequence.

37. The isolated protein of claim 36, wherein the heterologous polypeptide sequence is the Fc domain of an immunoglobulin.

38. The isolated protein of claim 35, wherein said protein is pegylated.

39. A composition comprising the protein of claim 35, and a pharmaceutically acceptable carrier.

40. An isolated protein of claim 35, produced by a method comprising:
  (a) synthesizing the protein of claim 35 in a cell; and
  (b) recovering the protein.

41. An isolated protein comprising a polypeptide sequence which is at least 90% identical to amino acid residues 1 to 132 of SEQ ID NO:2, wherein said isolated protein is capable of inhibiting cellular growth.

42. The isolated protein of claim 41, wherein said polypeptide sequence is at least 95% identical to amino acid residues 1 to 132 of SEQ ID NO:2 and is capable of inhibiting cellular growth.

43. The isolated protein of claim 41, wherein said isolated protein is capable of inhibiting endothelial cell growth.

44. The isolated protein of claim 43, wherein said isolated protein is capable of inhibiting venous endothelial cell growth.

45. The isolated protein of claim 41, wherein said isolated protein is capable of inhibiting epithelial cell growth.

46. The isolated protein of claim 45, wherein said isolated protein is capable of inhibiting mammary epithelial cell growth.

47. An isolated protein comprising a polypeptide sequence which is at least 90% identical to the polypeptide encoded by the cDNA contained in ATCC Deposit No. 97287, wherein said isolated protein is capable of inhibiting cellular growth.

48. The isolated protein of claim 47, wherein said polypeptide sequence is at least 95% identical to the polypeptide encoded by the cDNA contained in ATCC Deposit No. 97287 and is capable of inhibiting cellular growth.

49. The isolated protein of claim 47, wherein said isolated protein is capable of inhibiting endothelial cellular growth.

50. The isolated protein of claim 49, wherein said isolated protein is capable of inhibiting venous endothelial cell growth.

51. The isolated protein of claim 47, wherein said isolated protein is capable of inhibiting epithelial cell growth.

52. The isolated protein of claim 51, wherein said isolated protein is capable of inhibiting mammary epithelial cell growth.

53. An isolated protein comprising a polypeptide sequence which is at least 90% identical to amino acid residues 1 to 132 of SEQ ID NO:2, wherein said isolated protein is capable of stimulating cellular differentiation.

54. The isolated protein of claim 53, wherein said polypeptide sequence is at least 95% identical to amino acid residues 1 to 132 of SEQ ID NO:2 and is capable of stimulating cellular differentiation.

55. The isolated protein of claim 53, wherein said isolated protein is capable of stimulating tumor cell differentiation.

56. An isolated protein comprising a polypeptide sequence which is at least 90% identical to the polypeptide encoded by the cDNA contained in ATCC Deposit No. 97287, wherein said isolated protein is capable of stimulating cellular differentiation.

57. The isolated protein of claim 56, wherein said polypeptide sequence is at least 95% identical to the polypeptide encoded by the cDNA contained in ATCC Deposit No. 97287 and is capable of stimulating cellular differentiation.

58. The isolated protein of claim 56, wherein said isolated protein is capable of stimulating tumor cell differentiation.

* * * * *

UNITED STATES PATENT AND TRADEMARK OFFICE
CERTIFICATE OF CORRECTION

PATENT NO.    : 6,746,674 B2
DATED         : June 8, 2004
INVENTOR(S)   : Ni et al.

It is certified that error appears in the above-identified patent and that said Letters Patent is hereby corrected as shown below:

Title page,
Item [62], Related U.S. Application Data, should read: -- [62] Division of application No. 09/043,646, filed Sep. 9, 1998 (now Pat. No. 6,329,169) which is a Nat'l Stage of Int'l application No. PCT/US95/12540, filed on Sep. 29, 1995 -- and
Item [56], References Cited, OTHER PUBLICATIONS should read:
"Ngo et al.," reference, "Computational Complexity, Protein Structure Prediction, and the Levinthal Paradox," The Protein Folding Problem and Tertiary Structure Prediction, Mertz et al., Birkhauser Boston, 433-506, 1994. --

Signed and Sealed this

First Day of February, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 731
<212> TYPE: DNA
<213> ORGANISM: human
<220> FEATURE:
<221> NAME/KEY: CDS
<222> LOCATION: (16)..(411)
<223> OTHER INFORMATION:

<400> SEQUENCE: 1

```
ggggaaaggg caagg atg gtg gag gct ttc tgt gct acc tgg aag ctg acc        51
              Met Val Glu Ala Phe Cys Ala Thr Trp Lys Leu Thr
                1               5                  10 aac agt cag aac ttt gat gag tac atg aag gct cta ggc gtg ggc ttt         99
Asn Ser Gln Asn Phe Asp Glu Tyr Met Lys Ala Leu Gly Val Gly Phe
             15                  20                  25 gcc act agg cag gtg gga aat gtg acc aaa cca acg gta att atc agt        147
Ala Thr Arg Gln Val Gly Asn Val Thr Lys Pro Thr Val Ile Ile Ser
         30                  35                  40 caa gaa gga gac aaa gtg gtc atc agg act ctc agc aca ttc aag aac        195
Gln Glu Gly Asp Lys Val Val Ile Arg Thr Leu Ser Thr Phe Lys Asn
 45                  50                  55                  60 acg gag att agt ttc cag ctg gga gaa gag ttt gat gaa acc act gca        243
Thr Glu Ile Ser Phe Gln Leu Gly Glu Glu Phe Asp Glu Thr Thr Ala
                 65                  70                  75 gat gat aga aac tgt aag tct gtt gtt agc ctg gat gga gac aaa ctt        291
Asp Asp Arg Asn Cys Lys Ser Val Val Ser Leu Asp Gly Asp Lys Leu
             80                  85                  90 gtt cac ata cag aaa tgg gat ggc aaa gaa aca aat ttt gta aga gaa        339
Val His Ile Gln Lys Trp Asp Gly Lys Glu Thr Asn Phe Val Arg Glu
         95                 100                 105 att aag gat ggc aaa atg gtt atg acc ctt act ttt ggt gat gtg gtt        387
Ile Lys Asp Gly Lys Met Val Met Thr Leu Thr Phe Gly Asp Val Val
    110                 115                 120 gct gtt cgc cac tat gag aag gca taaaaatgtc cctggtcggg gcttggaaga       441
Ala Val Arg His Tyr Glu Lys Ala
125                 130 gctcttcagt ttttctgttt cctcaagtct cagtgctatc ctattacaac atggctgatc      501
attaattaga aggttatcct tggtgtggag gtggaaaatg gtgatttaaa aacttgttac      561
tccaagcaac ttgcccaatt ttaatctgaa aatttatcat gttttataat ttgaattaaa      621
gttttgtccc ccccccttt tttttataaa caagtgaata catttttataa tttcttttgg      681 aatgtaaatc aaatttgaat aaaaatctta cacgtgaaaa aaaaaaaaaa                 731
```

<210> SEQ ID NO 2
<211> LENGTH: 132
<212> TYPE: PRT
<213> ORGANISM: human

<400> SEQUENCE: 2

```
Met Val Glu Ala Phe Cys Ala Thr Trp Lys Leu Thr Asn Ser Gln Asn
 1               5                  10                  15

Phe Asp Glu Tyr Met Lys Ala Leu Gly Val Gly Phe Ala Thr Arg Gln
             20                  25                  30

Val Gly Asn Val Thr Lys Pro Thr Val Ile Ile Ser Gln Glu Gly Asp
         35                  40                  45
```

```
Lys Val Val Ile Arg Thr Leu Ser Thr Phe Lys Asn Thr Glu Ile Ser
 50                  55                  60
Phe Gln Leu Gly Glu Glu Phe Asp Glu Thr Thr Ala Asp Asp Arg Asn
 65                  70                  75                  80
Cys Lys Ser Val Val Ser Leu Asp Gly Asp Lys Leu Val His Ile Gln
                 85                  90                  95
Lys Trp Asp Gly Lys Glu Thr Asn Phe Val Arg Glu Ile Lys Asp Gly
             100                 105                 110
Lys Met Val Met Thr Leu Thr Phe Gly Asp Val Val Ala Val Arg His
             115                 120                 125
Tyr Glu Lys Ala
     130
```

<210> SEQ ID NO 3
<211> LENGTH: 23
<212> TYPE: DNA
<213> ORGANISM: human

<400> SEQUENCE: 3
cgcggatccg tggaggcttt ctg                                      23

<210> SEQ ID NO 4
<211> LENGTH: 27
<212> TYPE: DNA
<213> ORGANISM: human

<400> SEQUENCE: 4
cgcaagcttt tatgccttct catagtg                                  27

<210> SEQ ID NO 5
<211> LENGTH: 26
<212> TYPE: DNA
<213> ORGANISM: human

<400> SEQUENCE: 5
gcggatcccg tggaggcttt ctgtgc                                   26

<210> SEQ ID NO 6
<211> LENGTH: 34
<212> TYPE: DNA
<213> ORGANISM: human

<400> SEQUENCE: 6
gcgcggatcc gccaccatgg tggaggcttt ctgt                          34

<210> SEQ ID NO 7
<211> LENGTH: 52
<212> TYPE: DNA
<213> ORGANISM: human

<400> SEQUENCE: 7
gcgctctaga tcaagcgtag tctgggacgt cgtatgggta tgccttatag tg      52

<210> SEQ ID NO 8
<211> LENGTH: 26
<212> TYPE: DNA
<213> ORGANISM: human

<400> SEQUENCE: 8
gcggtacctt atgccttctc atagtg                                   26